United States Patent
Takahashi

(10) Patent No.: US 11,955,740 B2
(45) Date of Patent: Apr. 9, 2024

(54) ELECTRIC WIRE CONNECTION STRUCTURE, ELECTRIC WIRE CONNECTION METHOD, MEDICAL DEVICE, AND METHOD FOR MANUFACTURING THE SAME

(71) Applicant: Hitachi Metals, Ltd., Tokyo (JP)

(72) Inventor: Ryuta Takahashi, Tokyo (JP)

(73) Assignee: PROTERIAL, LTD., Tokyo (JP)

( * ) Notice: Subject to any disclaimer, the term of this patent is extended or adjusted under 35 U.S.C. 154(b) by 125 days.

(21) Appl. No.: 17/835,530

(22) Filed: Jun. 8, 2022

(65) Prior Publication Data

US 2022/0399659 A1 Dec. 15, 2022

(30) Foreign Application Priority Data

Jun. 11, 2021 (JP) ................................. 2021-098349

(51) Int. Cl.
*H01R 12/53* (2011.01)
*A61M 39/10* (2006.01)
(Continued)

(52) U.S. Cl.
CPC ............. *H01R 12/53* (2013.01); *A61M 39/10* (2013.01); *H01R 43/0263* (2013.01); *H05K 1/11* (2013.01);
(Continued)

(58) Field of Classification Search
CPC .......... H01R 12/53; H01R 4/023; H05K 1/11; H05K 1/18; H05K 2201/09409; H05K 2201/09445; H05K 2201/10356
See application file for complete search history.

(56) References Cited

U.S. PATENT DOCUMENTS

| 3,794,522 A | * | 2/1974 | Mueller | ............... | H02G 1/1275 |
| | | | | | 134/1 |
| 4,152,826 A | * | 5/1979 | Mueller | ................... | H02G 1/16 |
| | | | | | 439/497 |

(Continued)

FOREIGN PATENT DOCUMENTS

JP S 63-034997 A 2/1988
JP S64H01-077988 A 3/1989
(Continued)

OTHER PUBLICATIONS

Japanese Office Action dated Sep. 20, 2022, in corresponding Japanese Patent Application No. 2021-098349, with an English translation thereof.

(Continued)

*Primary Examiner* — Sherman Ng
(74) *Attorney, Agent, or Firm* — MCGINN I.P. LAW GROUP, PLLC.

(57) ABSTRACT

An electric wire connection structure is composed of insulated electric wires each including a core and an insulation coating covering the core. The cores of the insulated electric wires are connected to pads provided on a substrate. The insulated electric wires are arranged along a predetermined alignment direction and arranged parallel to each other. The insulation coating is removed at a part in a longitudinal direction of each of the insulated electric wires to expose the core. Exposed portions of the cores are connected to the pads, respectively. Some of the insulated electric wires are configured in such a manner that the core is exposed in an area where the insulation coatings of adjacent ones of the other insulated electric wires in the alignment direction are not removed.

8 Claims, 8 Drawing Sheets

(51) Int. Cl.
*H01R 43/02* (2006.01)
*H05K 1/11* (2006.01)
*H05K 1/18* (2006.01)
*H01R 4/02* (2006.01)
*H01R 4/04* (2006.01)

(52) U.S. Cl.
CPC ....... *H05K 1/18* (2013.01); *A61M 2039/1022* (2013.01); *H01R 4/023* (2013.01); *H01R 4/04* (2013.01); *H05K 2201/094* (2013.01); *H05K 2201/09409* (2013.01); *H05K 2201/09445* (2013.01); *H05K 2201/10287* (2013.01); *H05K 2201/10356* (2013.01)

(56) References Cited

U.S. PATENT DOCUMENTS

| | | | | |
|---|---|---|---|---|
| 4,641,904 | A | * | 2/1987 | Kosugi ................ H01R 12/675 439/98 |
| 4,927,387 | A | * | 5/1990 | Eckler ................... H01R 12/79 29/857 |
| 5,912,435 | A | * | 6/1999 | Elsinger ................ H01R 12/62 174/117 F |
| 6,351,884 | B1 | * | 3/2002 | Damaschke ........... H01R 12/62 29/865 |
| 10,653,306 | B2 | | 5/2020 | Kimura |
| 10,993,304 | B2 | * | 4/2021 | Tsai ...................... F21V 23/001 |
| 2014/0220822 | A1 | * | 8/2014 | Keyser .................. H01R 12/53 439/607.46 |
| 2015/0214666 | A1 | * | 7/2015 | Schumacher ...... H01R 13/6477 29/846 |
| 2016/0351292 | A1 | * | 12/2016 | Toth ................... A61B 18/1492 |
| 2019/0216304 | A1 | | 7/2019 | Kimura |

FOREIGN PATENT DOCUMENTS

| | | |
|---|---|---|
| JP | H 05-067997 U | 9/1993 |
| JP | 2011-082042 A | 4/2011 |
| JP | 2011-096403 A | 5/2011 |
| JP | 2012-234624 A | 11/2012 |
| JP | 2017-228449 A | 12/2017 |
| WO | WO 2018/105391 A1 | 6/2018 |

OTHER PUBLICATIONS

Japanese Office Action, dated Feb. 7, 2023, in Japanese Application No. 2021-098349 and English Machine Translation thereof.

* cited by examiner

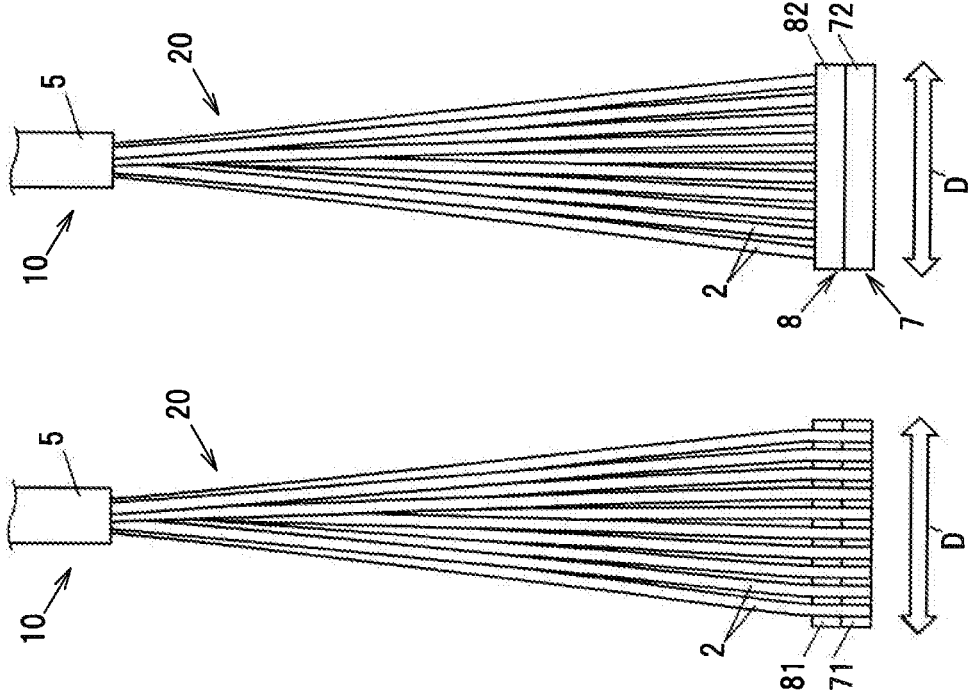
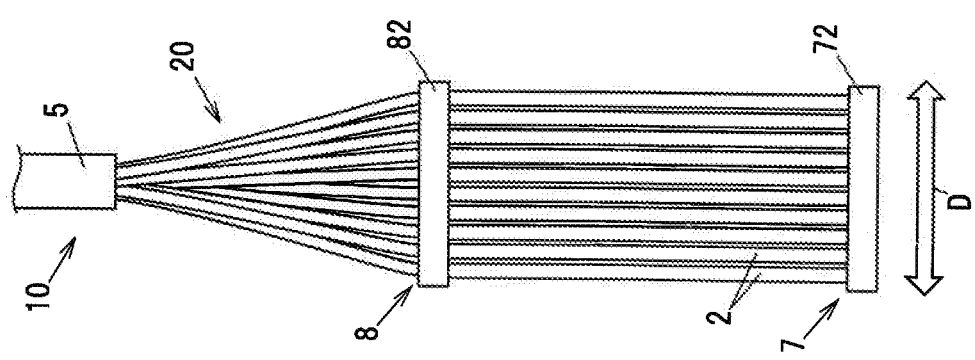
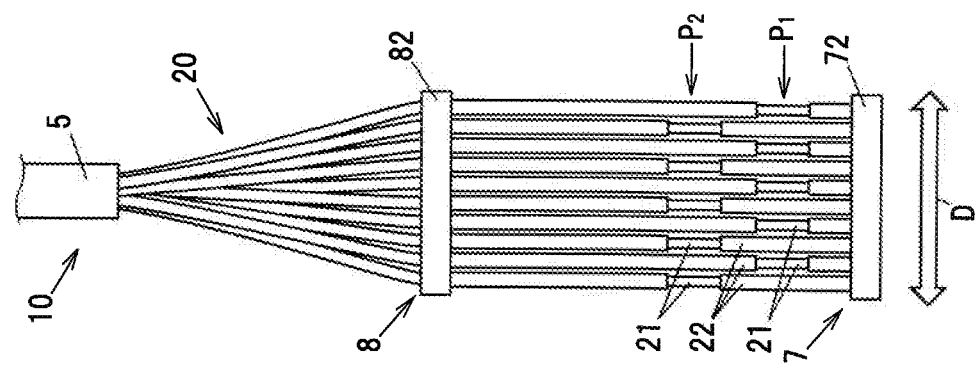

ELECTRIC WIRE CONNECTION STRUCTURE, ELECTRIC WIRE CONNECTION METHOD, MEDICAL DEVICE, AND METHOD FOR MANUFACTURING THE SAME

CROSS-REFERENCE TO RELATED APPLICATIONS

The present patent application claims the priority of Japanese patent application No. 2021-098349 filed on Jun. 11, 2021, and the entire contents thereof are hereby incorporated by reference.

TECHNICAL FIELD

The present invention relates to an electric wire connection structure, an electric wire connection method, a medical device and a method for manufacturing the medical device.

BACKGROUND ART

Conventionally, some medical catheter cables configured to be inserted into a human body for examination and treatment have a configuration in which multiple electrical wires are housed together in a tubular jacket. The multiple electrical wires are derived from the jacket at an end of a catheter cable, and connected to e.g., a substrate. Connection structures between the multiple electric wires and the substrate have been proposed as described in Patent Literatures 1 and 2.

The Patent Literature 1 shows a configuration in which multiple coaxial lines are divided into groups stacked in a thickness direction of a substrate, center conductors of respective groups of coaxial lines are connected to multiple contact conductors located on a surface of the substrate. A length of the coaxial line varies from group to group, and the center conductor is connected to the corresponding contact conductor of the substrate at each end of each coaxial line.

The Patent Literature 2 shows a configuration in which a core at an area where a jacket composed of an electrically insulating material is stripped off is inserted into a metal tube, and a connection land of the substrate is joined with the metal tube and the core by diffusion bonding or ultrasonic bonding while the metal tube being pressed from above, so as to improve the workability of connecting the core composed of a strand wire to the connection land of the substrate.

CITATION LIST

Patent Literature

Patent Literature 1: JP2011-82042A
Patent Literature 2: WO2018/105391

SUMMARY OF THE INVENTION

The catheter cable for medical use has been further reduced in diameter to reduce the burden on the human body. For example, a superfine electrical wire equivalent to AWG (American Wire Gauge) 46 is used, as described in the Patent Literature 1. However, as the electric wire becomes thinner, the difficulty of connecting the electric wires with the substrate increases.

Accordingly, it is an object of the invention to provide an electric wire connection structure, an electric wire connection method, a medical device and a method for manufacturing the medical device, in which a connection between multiple electric wires and a substrate can be facilitated.

So as to achieve the above object, one aspect of the invention provides an electric wire connection structure, comprising:
insulated electric wires each including a core and an insulation coating covering the core, the cores of the insulated electric wires being connected to pads provided on a substrate,
wherein the insulated electric wires are arranged along a predetermined alignment direction and arranged parallel to each other,
wherein the insulation coating is removed at a part in a longitudinal direction of each of the insulated electric wires to expose the core, and exposed portions of the cores are connected to the pads, respectively,
wherein at least one of the insulated electric wires is configured in such a manner that the core is exposed in an area where the insulation coatings of adjacent ones of other insulated electric wires in the alignment direction are not removed.

So as to achieve the object, another aspect of the invention provides an electrical wire connection method for connecting cores of insulated electric wires each including the core and an insulation coating covering the core with pads provided on a substrate, the method comprising:
aligning the insulated electric wires parallel to each other along a predetermined alignment direction;
removing the insulation coating to expose the core in a part in a longitudinal direction of each of the insulated electric wires; and
arranging the insulated electric wires in such a manner that the alignment direction is parallel to the substrate and connecting the exposed cores to the pads,
wherein at least one of the insulated electric wires is configured in such a manner that the core is exposed in an area where the insulation coatings of adjacent ones of other insulated electric wires in the alignment direction are not removed.

So as to achieve the above object, a further aspect of the invention provides a medical device, comprising:
a catheter cable comprising insulated electric wires each including a core and an insulation coating covering the core, and a substrate including pads connected to the cores of the insulated electric wires, one of both ends in a longitudinal direction of the catheter cable being configured to be inserted into a human body,
wherein the cores of the insulated electric wires are connected to the pads respectively by the electric wire connection structure as described above.

So as to achieve the above object, a still another aspect of the invention provides a method for manufacturing a medical device including a catheter cable including insulated electric wires each including a core and an insulation coating covering the core, and a substrate including pads connected to the cores of the insulated electric wires, one of both ends in a longitudinal direction of the catheter cable being configured to be inserted into a human body, the method comprising:
connecting the cores of the insulated electric wires to the pads respectively by the electric wire connection method as described above.

Effect of the Invention

According to the invention, it is possible to provide an electric wire connection structure, an electric wire connection method, a medical device and a method for manufacturing the medical device, in which a connection between multiple electric wires and a substrate can be facilitated.

BRIEF DESCRIPTION OF DRAWINGS

FIGS. 6A to 6C are explanatory diagrams showing an alignment step.

FIG. 6D is an explanatory diagram showing an insulation coating removal step.

BEST MODE FOR CARRYING OUT THE INVENTION

Embodiment

Figure 1A:
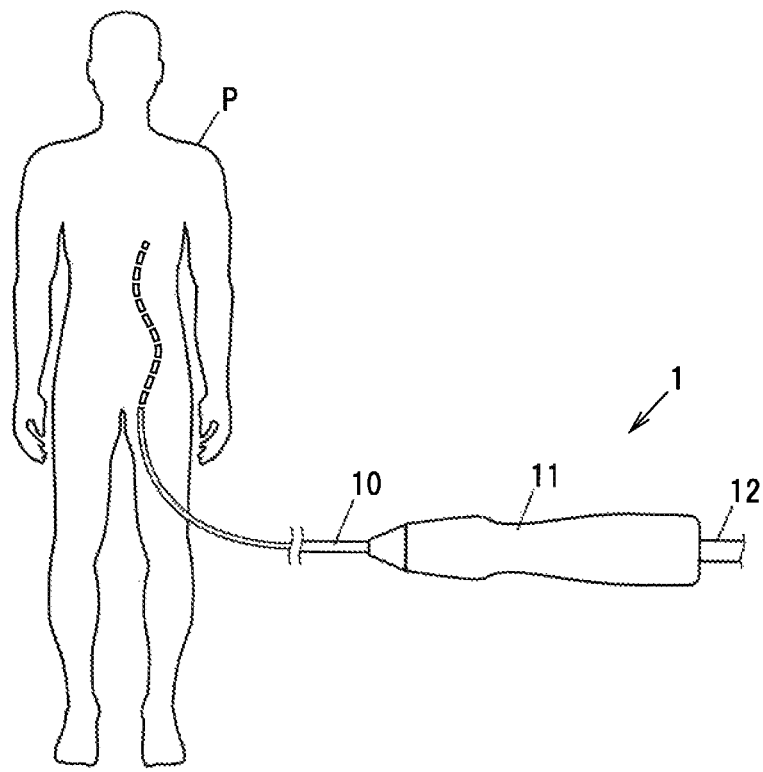
FIG. 1A is an explanatory diagram showing the state of use of a multi-electrode catheter as an example of a medical device according to the embodiment of the present invention.
Figure 1B:
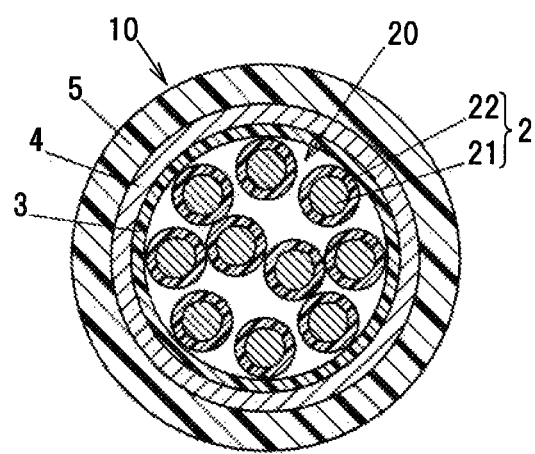
FIG. 1B is a cross-section view of a catheter cable.

FIG. 1A is an explanatory diagram showing the state of use of a multi-electrode catheter as an example of a medical device according to the embodiment of the present invention. FIG. 1B is a cross-section view of a catheter cable.

A multi-electrode catheter 1 includes a catheter cable 10 and a handle 11 configured to be operated by a physician or other operator. The catheter cable 10 includes one end in a longitudinal direction which is housed in the handle 11, and the other end in the longitudinal direction which is inserted into a human body of a patient (subject) P to be examined or treated. FIG. 1A shows the catheter cable 10 in the human body of the patient P with a dashed line.

As shown in FIG. 1B, the catheter cable 10 includes an electric wire bundle 20 composed of multiple insulated electric wires 2, a binding tape 3 wrapped around an outer periphery of the electric wire bundle 20, a shield conductor 4 provided around an outer periphery of the binding tape 3, and a tubular jacket 5 provided around an outer periphery of the shield conductor 4. The jacket 5 is composed of e.g., fluorine resin, which houses the electric wire bundle 20, the binding tape 3, and the shield conductor 4. In the present embodiment, 10 pieces of the insulated electric wires 2 are bundled together to form the electric wire bundle 20. It is also possible to place a fibrous or strip-like filler between the multiple insulated electric wires 2 inside the binding tape 3.

The insulated electric wire 2 includes a core (i.e., a core wire) 21, which is composed of copper and other good conductive metals, and an insulation coating 22 covering the core 21. In the present embodiment, the insulated electric wire 2 is composed of an enamel wire, and the core 21 is composed of a single wire having a circular cross-section and covered by the insulation coating 22, which is composed of a resin composition such as polyurethane. An outer diameter of the core 21 is 0.02 mm or more and 0.10 mm or less. In the present embodiment, the core 21 is equivalent to AWG48 according to American Wire Gauge (AWG) standards, with a conductor diameter of 0.032 mm. A thickness of the insulation coating 22 is 0.008 mm.

The multiple electric wires 2 are derived from the jacket 5 into the handle 11. From the handle 11, a console cable 12, which is thicker than the catheter cable 10, is derived. The console cable 12 connects the handle 11 to a console (not shown). The console is an information processing device equipped with a microprocessor, memory, etc., and it amplifies signals transmitted by the human body of the patient P via the multiple insulated electric wires 2, for example, and outputs an image signal to display the status inside the body of the patient P obtained by the amplified signals on the display.

The handle 11 houses a substrate with multiple pads connected to the cores 21 of the multiple insulated electric wires 2. The signals from the human body of the patient P are relayed by this substrate and sent to the console by the console cable 12. The following describes the electric wire connection structure in which the cores 21 of the multiple insulated electric wires 2 are connected to multiple pads of the substrate.

Figure 2A:
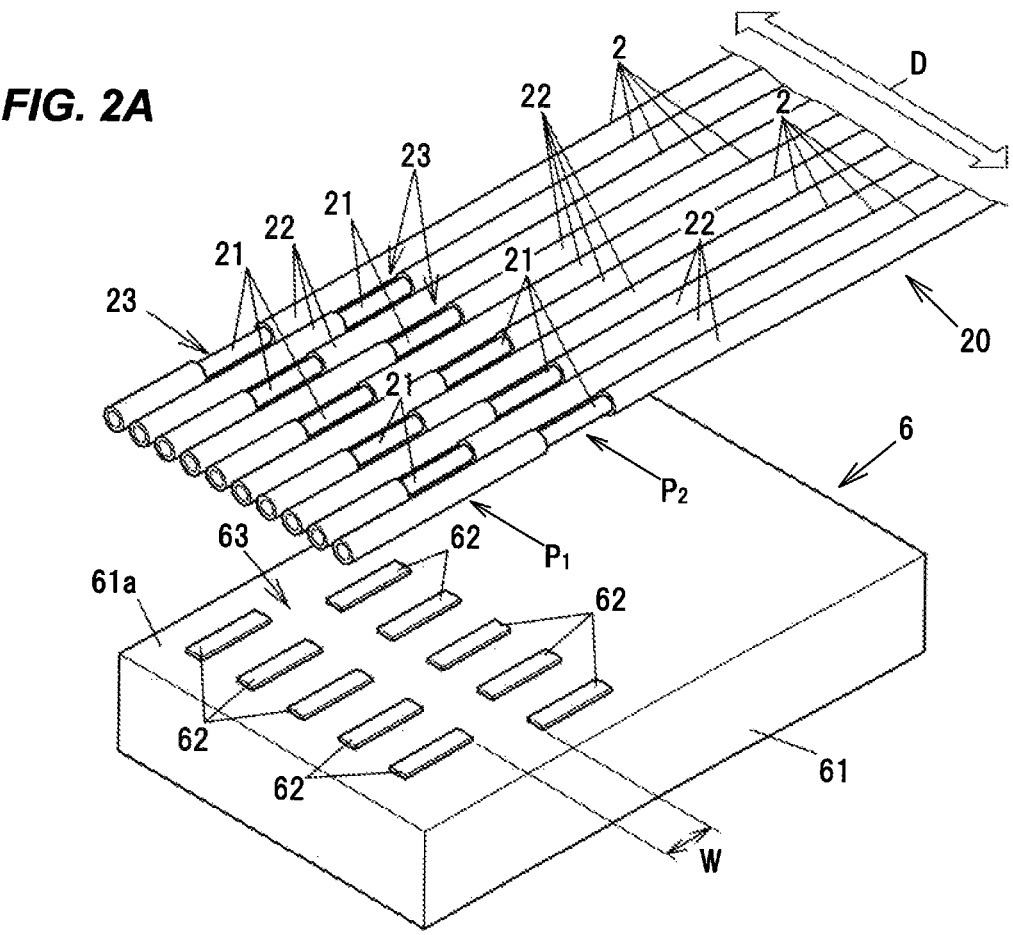
FIGS. 2A and 2B are perspective view showing parts of the multiple insulated electric wires and a substrate to be accommodated in a handle.
Figure 2B:
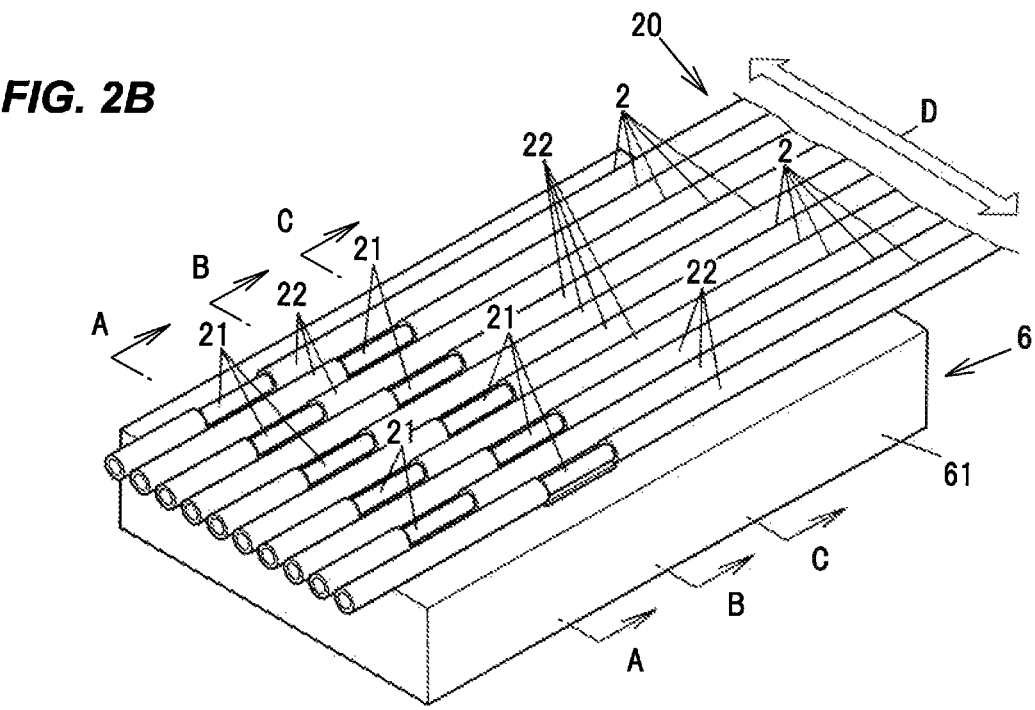
Figure 3A:
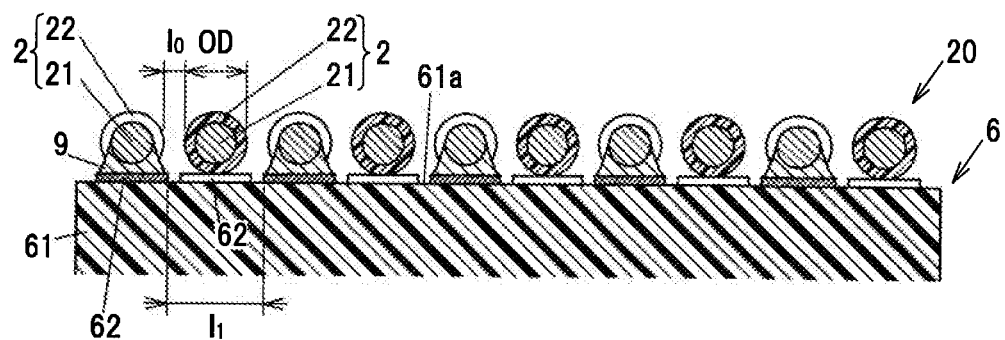
FIGS. 3A to 3C are cross-sectional views taken along an A-A line, a B-B line, and a C-C line in FIG. 2B.
Figure 3B:
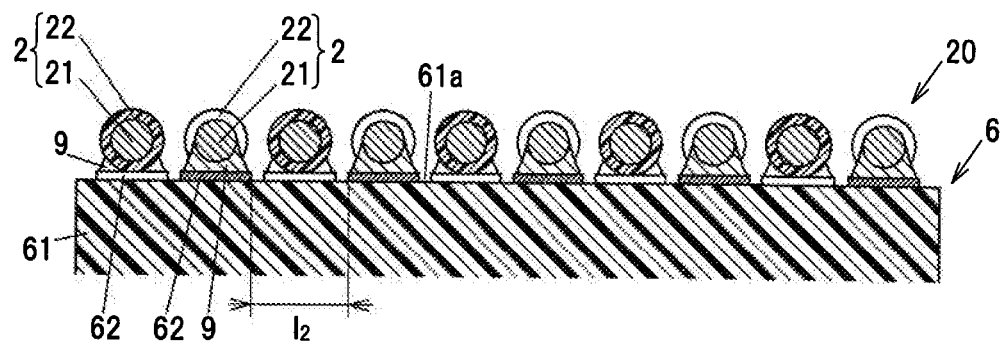
Figure 3C:
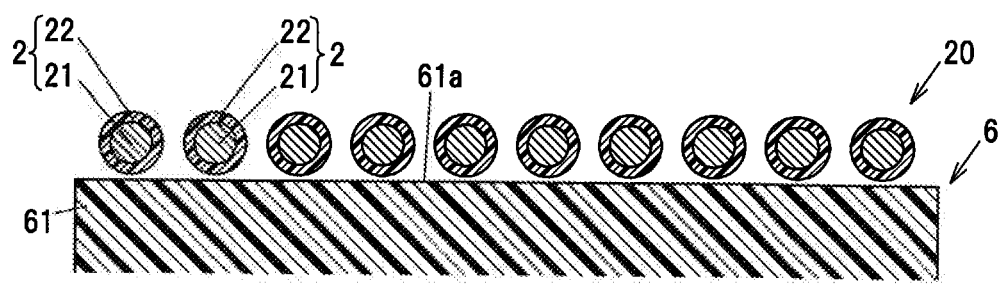

FIGS. 2A and 2B are perspective view showing parts of the multiple insulated electric wires 2 and a substrate 6 to be accommodated in the handle 11. FIG. 2A shows the multiple insulated electric wires 2 and the substrate 6 that are located at positions opposed to each other, and FIG. 2B shows that the cores 21 of the multiple insulated electric wires 2 are connected to multiple pads 62 on the substrate 6. FIGS. 3A to 3C are cross-sectional views taken along an A-A line, a B-B line, and a C-C line in FIG. 2B.

The substrate 6 includes a flat-shaped base member 61 composed of an insulator such as polyimide, and the multiple pads 62 are provided on a first main surface 61a of the base member 61. Each of the multiple pads 62 is a rectangular metal foil that attaches to the first main surface 61a of the base member 61. It should be noted that the substrate 6 is provided with a wiring pattern extending from the multiple pads 62, a through hole that penetrates the base member 61 in the thickness direction, and the like, but these elements are not shown in FIGS. 2A and 2B.

The front and rear sections, including connection points with the multiple pads 62, of the multiple insulated electric wires 2 are arranged along a predetermined alignment direction D which is parallel to the substrate 6, and also arranged parallel to each other. In FIGS. 2A and 2B, this alignment direction D is indicated by double arrows. In addition, the insulation coating 22 is removed (i.e., stripped off) at a part in the longitudinal direction of each of the multiple insulated electric wires 2 to expose the core 21, and exposed portions 23 of the cores 21 are connected to the multiple pads 62, respectively.

Some of the multiple insulated electric wires 2 are configured in such a manner that the core 21 is exposed in the area where the insulation coatings 22 of the adjacent ones of the other insulated electric wires 2 in the alignment direction D are not removed (i.e., stripped off). In the present embodiment, the exposed portions 23 of the cores 21 are alternately aligned at a first position $P_1$ and a second position $P_2$, with a predetermined interval W in a direction perpendicular to the alignment direction D (i.e., a longitudinal direction of the insulated electric wires 2), and staggered along the alignment direction D. More specifically, five insulated electric wires 2 with the cores 21 exposed at the first position $P_1$ and five insulated electric wires 2 with the cores 21 exposed at the second position $P_2$ are alternately aligned along the alignment direction D.

As shown in FIG. 3A, an interval $I_0$ of the multiple insulated electric wires 2 in the alignment direction D is less than an outer diameter OD of the insulated electric wire 2. The interval $I_0$ is 20% to 80% of the outer diameter OD of the insulated electric wire 2, for example. As mentioned above, when the core 21 has the outer diameter of 0.032 mm (32 μm) and the insulation coating 22 has a thickness of 0.008 mm (8 μm), the OD of the insulated electric wire 2 is 0.048 mm (48 μm). In addition, the relative misalignment in the alignment direction D between the respective insulated electric wires 2 and the substrate 6 is allowed in the range where the exposed core 21 and the pad 62 face to each other in the thickness direction of the substrate 6. If the interval $I_0$ in the alignment direction D of the multiple insulated electric wires 2 is not uniform, the mean value of the intervals $I_0$ should be less than the outer diameter OD of the insulated electric wire 2.

As shown in FIG. 3A, an interval $I_1$ of two pads 62 adjacent to each other along the alignment direction D at the first longitudinal position $P_1$ of the insulated electric wire 2 is greater than the outer diameter OD of the insulated electric wire 2. Also, as shown in FIG. 3B, an interval $I_2$ of two pads 62 adjacent to each other along the alignment direction D at the second longitudinal position $P_2$ of the insulated electric wire 2 is greater than the outer diameter OD of the insulated electric wire 2.

Figure 7:
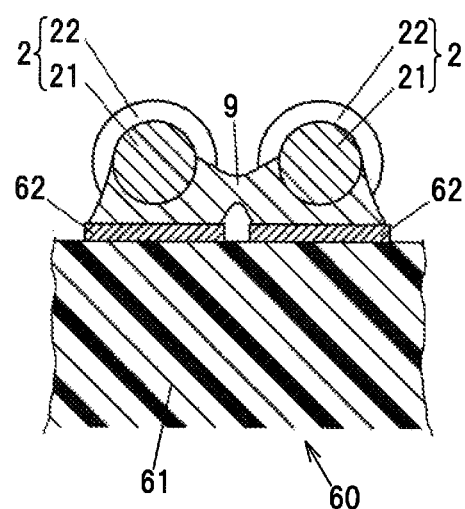
FIG. 7 is a cross-sectional view showing an electric wire connection structure in a comparative example.

As shown in FIG. 2A, a pad-free area (an area where the pad 62 is unformed) 63 with a predetermined width W is provided between the pads 62 to be connected to the exposed cores 21 at the first position $P_1$ and the pads 62 to be connected to the exposed cores 21 at the second position $P_2$. The width W is a dimension that can suppress the formation of a solder bridging between the multiple pads 62 sandwiching the pad-free area 63, as shown in FIG. 7 to be described later.

In the longitudinal direction of the insulated electric wire 2, the exposed portion 23 is formed in the area except a tip end (i.e., a leading edge, a distalmost end) of each of the multiple insulated electric wires 2. In other words, at the tip end of the insulated electric wire 2, the core 21 is covered with the insulation coating 22. The tip end of the insulated electric wire 2 is the part configured to be grasped (i.e., held) by jigs (to be described later) when connecting the exposed core 21 to the pad 62 on the substrate 6. The following describes an electric wire connection method for connecting the cores 21 of the multiple insulated electric wires 2 to the multiple pads 62 of the substrate 6.

This electrical wire connection method includes an alignment step of arranging the multiple insulated electric wires 2 parallel to each other along the alignment direction D, an insulation coating removal step of stripping the insulation coating 22 off to expose the core 21 in a part in the longitudinal direction of each of the multiple insulated electric wires 2, and a connection step of arranging the multiple insulated electric wires 2 in such a manner that the alignment direction D is parallel to the substrate 6 and connecting the exposed cores 21 to the multiple pads 62.

Figure 4:
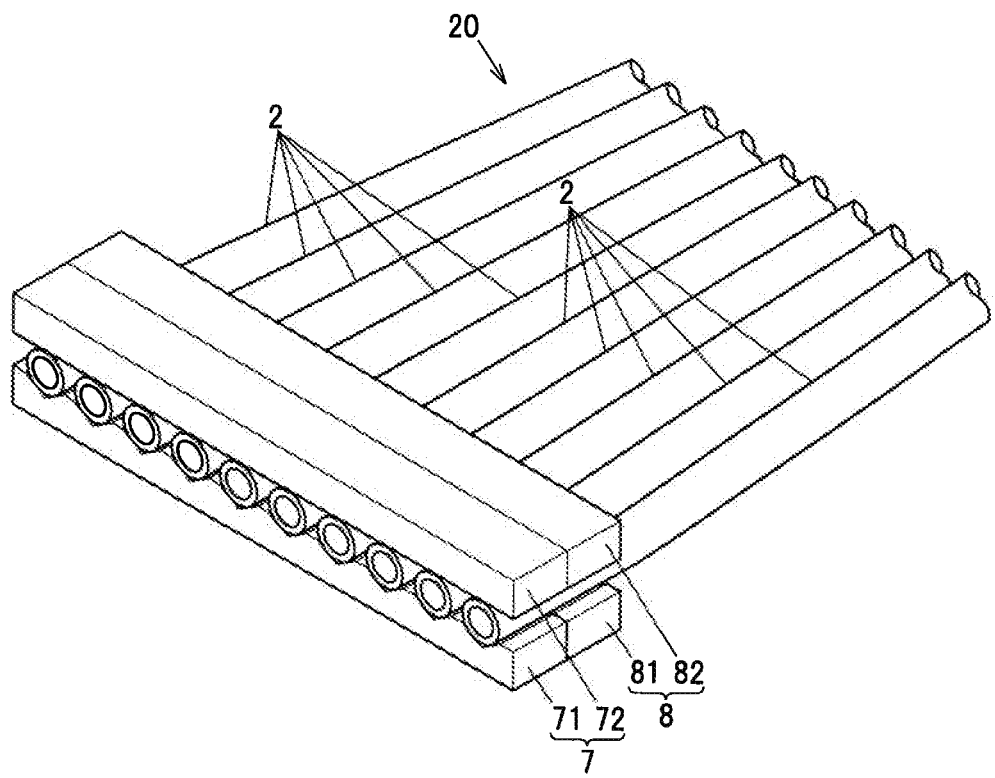
FIG. 4 is a perspective view showing the multiple insulated electric wires being grasped by first and second jigs.

FIG. 4 is a perspective view showing the multiple insulated electric wires 2 being grasped (held) by first and second jigs 7 and 8. The first and second jigs 7, 8 respectively have lower holders 71, 81 and upper holders 72, 82, and the multiple insulated electric wires 2 are grasped between the lower holders 71, 81 and the upper holders 72, 82.

Figure 5:
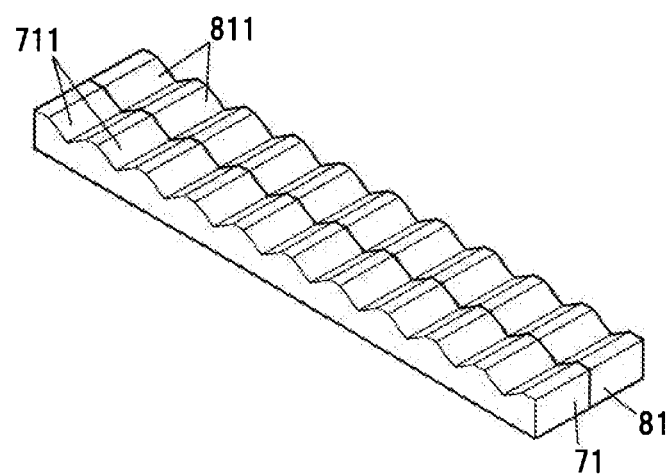
FIG. 5 is a perspective view showing lower holders of the first and second jigs.

FIG. 5 is a perspective view showing the lower holders 71, 81 in the first and second jigs 7, 8. The lower holder 71 of the first jig 7 is formed with multiple grooves 711 to grasp the multiple insulated electric wires 2 equidistantly (i.e., at regular intervals). The lower holder 81 of the second jig 8 is also formed with an equal number of grooves 811. The shape of each of the grooves 711 and 811 as seen from the longitudinal direction of the multiple insulated electric wires 2 is a V-shape as shown in FIG. 5, as an example. The upper holders 72, 82 of the first and second jigs 7, 8 respectively have flat opposite surfaces with respect to the lower holders 71, 81, and hold the multiple insulated electric wires 2 between the lower holders 71, 81 and the upper holders 72, 82. The upper holders 72, 82 may be also formed with multiple grooves similar to the lower holders 71, 81.

FIGS. 6A to 6C are explanatory diagrams showing the alignment step. FIG. 6A shows the first stage of the alignment step. In this first stage, the jacket 5 provided at one end of the catheter cable 10 is removed together with the binding tape 3 and the shield conductor 4 to expose the electric wire bundle 20, and the insulated electric wires 2 are accommodated in each of the lower grooves 711, 811 of the lower holders 71, 81 of the first and second jigs 7, 8.

In the second stage of the alignment step, the multiple insulated electric wires 2 are sandwiched between the lower holders 71, 81 and the upper holders 72, 82, as shown in FIG. 6B. The first jig 7 grasps the respective tip ends of the multiple insulated electric wires 2, while the second jig 8 grasps the multiple insulated electric wires 2 on a jacket 5-side (i.e., on the side closer to the jacket 5) of the first jig 7. In the example shown in FIG. 6B, the second jig 8 grasps the multiple insulated electric wires 2 at a position adjacent to the first jig 7.

In the third stage of the alignment step, as shown in FIG. 6C, the second jig 8 moves toward the jacket 5 while the first jig 7 holds the tip ends of the multiple insulated electric wires 2, thereby increasing a distance between the first jig 7 and the second jig 8. This will make the multiple insulated electric wires 2 be held at two points, i.e., a first point at the tip end in the longitudinal direction and a second point distant from the tip end in the longitudinal direction. When moving the second jig 8, a gripping force of the second jig 8 is adjusted to the extent that it is possible to slide the second jig 8 along the longitudinal direction of the multiple insulated electric wires 2 without detaching the insulated electric wires 2 from the grooves 811 of the lower holder 81.

FIG. 6D is an explanatory diagram showing the insulation coating removal step. In the insulation coating removal (i.e., stripping) step, the core 21 of some of the insulated electric wires 2 is exposed in the area where the insulation coatings 22 of the other two adjacent insulated electric wires 2 in the alignment direction D are not removed. In the present embodiment, the core 21 is exposed in the area where the insulation coatings 22 of the other two adjacent insulated electric wires 2 in the alignment direction D are not removed, except for the two insulated electric wires 2 that are provided both side ends in the alignment direction D. As a result, the areas where the cores 21 are exposed are formed in a staggered pattern.

The method of removing the insulation coating 22 is not limited. The insulation coating 22 may be removed in the longitudinal part of the insulated electric wire 2 by e.g., irradiating laser light. In the insulation coating removal step, the insulation coating 22 may be stripped off entirely around the insulated electric wire 2, but only the insulation coating 22 in the area facing the pad 62 may be removed. The core 21 can still be connected to the pad 62. However, if the insulation coating 22 is removed entirely around the insulated electric wire 2, it will be easier to connect the core 21 to the pad 62 in the connection step and to check the connection between the core 21 and the pad 62.

In the connection step, between the two longitudinal points of the insulated electric wire 2 grasped in the first and second jigs 7, 8, the cores 21 of the multiple insulated electric wires 2 are connected to the multiple pads 62 respectively. The connection between the core 21 and the pad 62 may be soldered, but an electrically conductive adhesive may be also used to connect the core 21 to the pad 62. When the core 21 and the pad 62 are connected by soldering, for example, the core 21 can be connected to the pad 62 by making contact the core 21 with a cream solder previously applied to the pad 62 and then heating the cream solder and melting it.

FIGS. 3A and 3B show the cores 21 and the pads 62 being connected by a solder 9. A heat-resistant temperature of the insulation coating 22 is higher than a melting point of the solder 9. When soldering the core 21 of the insulated electric wire 2, the insulation coating 22 will not melt even if the molten solder contacts with the insulation coatings 22 of the two other insulated electrical wires 2 adjacent to the target insulated electric wire 2.

As shown in FIGS. 3A and 3B, between the two pads 62 adjacent to each other along the alignment direction D at the first position $P_1$, there is a portion coated with the insulation coating 22 of the insulated electric wire 2, which is connected to the pad 62 at the second position $P_2$. At the second position P2, between the two pads 62 adjacent to each other along the alignment direction D, there is a portion coated with the insulation coating 22 of the insulated electric wire 2, which is connected to the pad 61 at the first position $P_1$. By providing the insulation coating 22 of the insulated electric wire 2 to be interposed between the two pads 62 adjacent to each other along the alignment direction D, it is possible to suppress the flow of the molten solder and to suppress the occurrence of solder bridging (short-circuit).

In the connection step, the cores 21 of the multiple insulated electric wires 2 are connected to the multiple pads 62 respectively, while a longitudinal tension is applied to the multiple insulated electric wires 2. By applying the tension to the multiple insulated electric wires 2, it is possible to suppress the sagging of the insulated electric wires 2 which may cause the misalignment between the cores 21 and the pads 62.

Comparative Example

FIG. 7 is a cross-sectional view showing a comparative example where the cores 21 of a pair of the insulated electric wires 2 being arranged parallel to each other are exposed at a position aligned to the alignment direction of the insulated electric wires 2 and soldered to the pads 62 of the substrate 60. When the cores 21 are soldered in this way, an interval between the adjacent pads 62 is reduced, and the solder bridging is more likely to occur as shown in FIG. 7.

Effect of the Embodiment

According to the embodiment as described above, in the cores 21 of the multiple insulated electric wires 2, the portions exposed from the insulation coatings 22 are not adjacent to each other in the alignment direction D, so that the intervals $I_1$, $I_2$ between the pads 62 in the alignment direction D can be enlarged to be greater than the outer diameter OD of the insulated electric wire 2, thereby suppressing the occurrence of the solder bridging. This makes it easy to connect the cores 21 of the multiple insulated electric wires 2 to the pads 62. It is also possible to automate the connection between the core 21 and the pad 62, not just the manual connection.

Modified Example 1

Figure 8A:
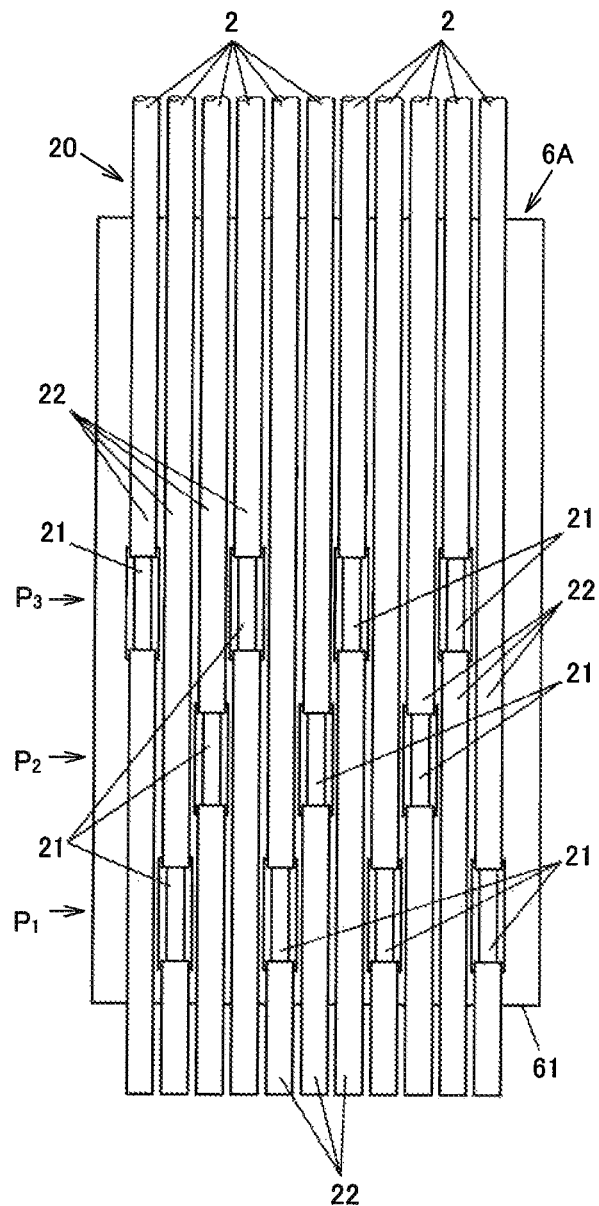
FIG. 8A is a schematic diagram showing an electric wire connection structure in a modified example 1.
Figure 8B:
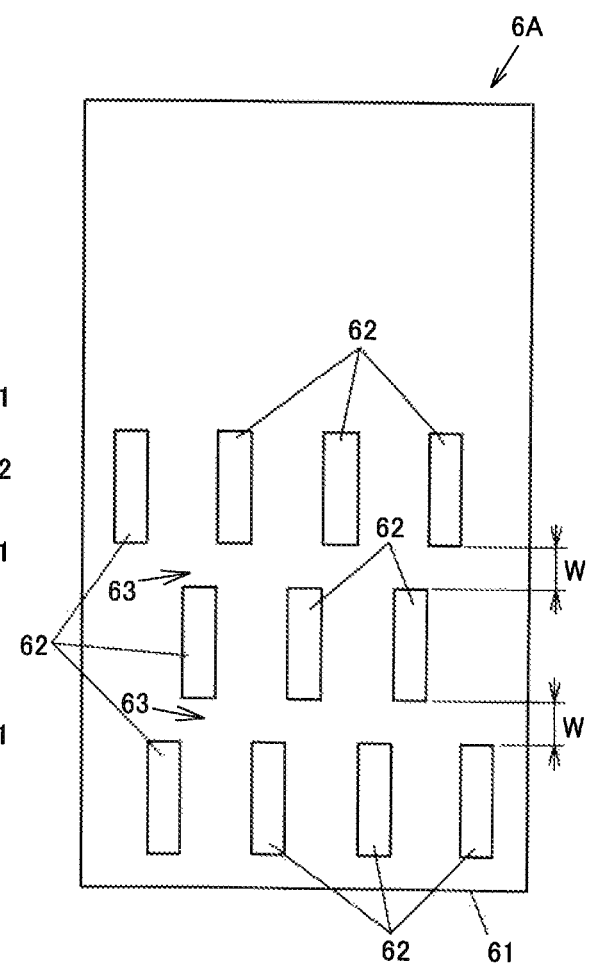
FIG. 8B is a plan view showing the substrate in the modified example 1.

FIG. 8A is a schematic diagram showing an electric wire connection structure in a modified example 1. FIG. 8B is a plan view showing a substrate 6A in the modified example 1. In the above embodiment, the connection structure for connecting the core 21 of 10 pieces of the insulated electric wires 2 to the pads 62 of the substrate 6 was explained. In this modified example 1, the cores 21 of 11 pieces of the insulated electric wires 2 are connected to the pads 62 of the substrate 6A. In the above embodiment, we explained that the cores 21 are exposed at the first position $P_1$ and the second position $P_2$ in the longitudinal direction of the multiple insulated electric wires 2. In the modified example 1, the cores 21 are exposed at the first position $P_1$, the second position $P_2$, and a third position $P_3$ in the longitudinal direction of the multiple insulated electric wires 2.

As shown in FIG. 8A, four of the 11 pieces of the insulated electric wires 2 have the cores 21 exposed from the insulation coatings 22 at the first position $P_1$. The other three insulated electric wires 2 have the cores 21 exposed from the insulation coatings 22 at the second position $P_2$, and the remaining four insulated electric wires 2 have the cores 21 exposed from the insulation coatings 22 at the third position $P_3$. At the first position $P_1$, the second position $P_2$, and the third position $P_3$, the multiple insulated electric wires 2 are arranged parallel to each other in such a manner that the exposed portions of the cores 21 are not adjacent to each other in the alignment direction D.

The substrate 6A has the pads 62 with a number equal to the number of insulated electric wires 2, at a position corresponding to the exposed position of the cores 21, as shown in FIG. 8B. Between the pads 62 to be connected to the cores 21 exposed at the first position $P_1$ and the pads 62 to be connected to the cores 21 exposed at the second position $P_2$, and between the pads 62 to be connected to the cores 21 exposed at the second position $P_2$ and the pads 62 to be connected to the cores 21 exposed at the third position $P_3$, the pad-free areas 63 with a predetermined width are provided respectively.

As with the present modified example 1, in the cores 21 of the multiple insulated electric wires 2, the portions exposed from the insulation coatings 22 are not adjacent to each other in the alignment direction D, so that the intervals between the pads 62 in the alignment direction D can be enlarged, thereby suppressing the occurrence of the solder bridging. This makes it easy to connect the cores 21 of the multiple insulated electric wires 2 to the pads 62.

Further, in the electrical wire connection structure in modified example 1, the multiple insulated electric wires 2 are aligned parallel to each other, some of the insulation coatings 22 are removed, the cores 21 are exposed, and the exposed cores 21 are connected to the pads 62 respectively, by the same alignment step, insulation coating removal step, and connection step as those in the above embodiment. The same applies to a modified example 2 to be described below.

Modified Example 2

Figures 9A, 9B:
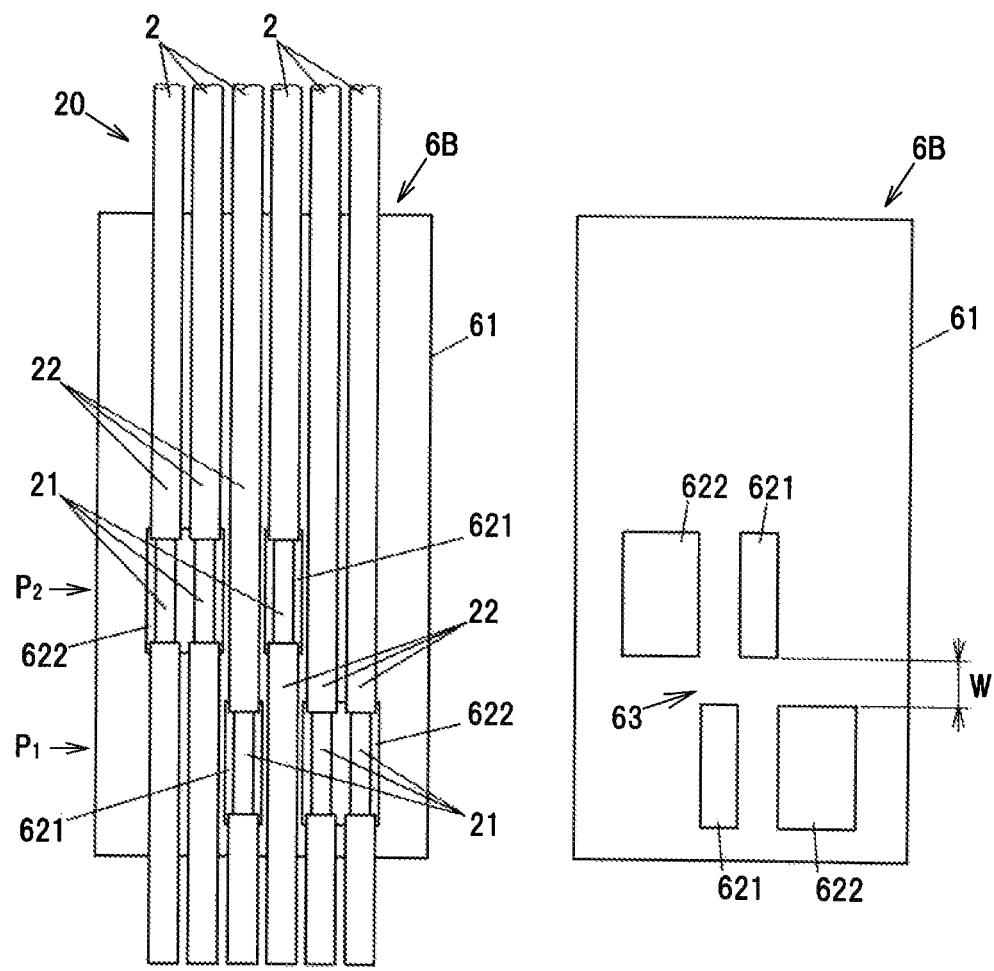
FIG. 9A is a schematic diagram showing an electric wire connection structure in a modified example 2.
FIG. 9B is a plan view showing the substrate in the modified example 2.

FIG. 9A is a schematic diagram showing an electric wire connection structure in the modified example 2. FIG. 9B is a plan view showing a substrate 6B in the modified example 2. In the above embodiment, it was explained that the pads 62 of the same size are staggered at the first position $P_1$ and the second position $P_2$. In the modified example 2, several types of pads with different widths in the alignment direction D (narrow pads 621 and wide pads 622) are provided on the substrate 6B. In the modified example 2, the cores 21 of 6 pieces of the insulated electric wires 2 are connected to the narrow pads 621 and the wide pads 622 on the substrate 6B.

The narrow pad 621 is formed to have approximately the same width as the outer diameter of the insulated electric wire 2, similar to the pad 62 on the substrate 6 in the above embodiment. The wide pad 622 is formed about twice as wide as the narrow pad 621. On the substrate 6B, one narrow pad 621 and one wide pad 622 are provided at the sites corresponding to the first position $P_1$ and the second position $P_2$ in the longitudinal direction of the multiple insulated electric wires 2.

Three of the 6 pieces of the insulated electric wires 2 have the cores 21 exposed from the insulation coatings 22 at the first position $P_1$. The other three insulated electric wires 2 have the cores 21 exposed from the insulation coatings 22 at the second position $P_2$. Of the three insulated electric wires 2 with the cores 21 exposed at the first position $P_1$, one core 21 of the insulated electric wires 2 is connected to the narrow pad 621, and the other two cores 21 of the insulated electric wires 2 are connected to the wide pad 622 together. Of the three insulated electric wires 2 with the cores 21 exposed at the second position $P_2$, one core 21 of the insulated electric wires 2 is connected to the narrow pad 621, and the other two cores 21 of the insulated electric wires 2 are connected to the wide pad 622 together.

The insulated electric wire 2 with the core 21 being connected to the wide pad 622 is used to supply power to electronic devices inserted into the human body, e.g., CCD cameras. In addition, the insulated electric wire 2 with the core 21 connected to the narrow pad 621 is used as a signal line to transmit signals such as input signals to or output signals from e.g., electronic devices.

As with the modified example 2, in the insulated electric wire 2 with the core 21 connected to the narrow pad 621, the exposed portion of the core 21 is not adjacent to the exposed portions of the cores 21 in the other insulated electric wires 2 along the alignment direction D, so as with the above embodiment, it will be possible to easily connect the cores 21 of the insulated electric wires 2 with the narrow pad 621 and the wide pad 622 on the substrate 6B.

Summary of the Embodiment

Next, the technical concept grasped from the above-described embodiment is described with reference to the signs or the like in the embodiment. However, each sign or the like in the following description is not limited to a member or the like specifically showing the elements in the following claims in the embodiment.

As to the feature [1], an electric wire connection structure includes insulated electric wires 2 each including a core 21 and an insulation coating 22 covering the core 21, the cores 21 of the insulated electric wires 2 being connected to pads 62, 621, 622 provided on a substrate 6, 6A, 6B, wherein the insulated electric wires 2 are arranged along a predetermined alignment direction D and arranged parallel to each other, wherein the insulation coating 22 is removed at a part in a longitudinal direction of each of the insulated electric wires 2 to expose the core 21, and exposed portions 23 of the cores 21 are connected to the pads 62, respectively, wherein some of the insulated electric wires 2 are configured in such a manner that the core 21 is exposed in an area where the insulation coatings 22 of adjacent ones of other insulated electric wires 2 in the alignment direction D are not removed.

As to the feature [2], in the electric wire connection structure described in the feature [1], an interval $I_0$ of the insulated electric wires 2 in the alignment direction D is less than an outer diameter OD of the insulated electric wire 2.

As to the feature [3], in the electric wire connection structure described in the feature [2], an outer diameter of the core 21 is 0.10 mm or less.

As to the feature [4], in the electric wire connection structure described in any one of the features [1] to [3], the exposed portions 23 of the cores 21 are alternately aligned at a first position $P_1$ and a second position $P_2$, with a predetermined interval W in a direction perpendicular to the alignment direction D.

As to the feature [5], in the electric wire connection structure described in any one of the features [1] to [4], the exposed portion 23 of the core 21 is formed in an area except a tip end of each of the insulated electric wires 2.

As to the feature [6], an electrical wire connection method, for connecting cores 21 of insulated electric wires 2 each including the core 21 and an insulation coating 22 covering the core 21 with pads 62, 621, 622 provided on a substrate 6, 6A, 6B, includes an alignment step of aligning the insulated electric wires 2 parallel to each other along a predetermined alignment direction D, an insulation coating removal step of removing the insulation coating 22 to expose the core 21 in a part in a longitudinal direction of each of the insulated electric wires 2, and a connection step of arranging the insulated electric wires 2 in such a manner that the alignment direction D is parallel to the substrate 6, 6A, 6B and connecting the exposed cores 21 to the pads 62, 621, 622, wherein some of the insulated electric wires 2 are configured in such a manner that the core 21 is exposed in an area where the insulation coatings 22 of adjacent ones of the other insulated electric wires 2 in the alignment direction D are not removed.

As to the feature [7], in the electric wire connection method described in the feature [6], the cores 21 of the insulated electric wires 2 are connected to the pads 62, 621, 622 respectively, while a longitudinal tension is applied to the insulated electric wires 2.

As to the feature [8], in the electric wire connection method described in the feature [7], in the alignment step, the insulated electric wires 2 are held at a first point at a tip end in the longitudinal direction and a second point distant from the tip end in the longitudinal direction, and, in the connection step, the cores 21 of the insulated electric wires 2 are connected to the pads 62, 621, 622 respectively between the first point and the second point.

As to the feature [9], a medical device (e.g., a multi-electrode catheter 1) includes a catheter cable 10 including insulated electric wires 2 each including a core 21 and an insulation coating 22 covering the core 21, and a substrate 6 including pads 62, 621, 622 connected to the cores 21 of the insulated electric wires 2, wherein one of both ends in a longitudinal direction of the catheter cable 10 is configured to be inserted into a human body, wherein the respective cores 21 of the insulated electric wires 2 are connected to the pads 62, 621, 622 by the electric wire connection structure described in any one of the features [1] to [5].

As to the feature [10], a method for manufacturing a medical device (e.g., a multi-electrode catheter 1) including a catheter cable 10 including insulated electric wires 2 each including a core 21 and an insulation coating 22 covering the core 21, and a substrate 6 including pads 62, 621, 622 connected to the cores 21 of the insulated electric wires 2, wherein one of both ends in a longitudinal direction of the catheter cable 10 is configured to be inserted into a human body, includes connecting the respective cores 21 of the insulated electric wires 2 to the pads 62, 621, 622 by the electric wire connection method described in any one of the features [6] to [8].

As described above, the embodiment of the present invention is explained, but the embodiment described above does not limit the invention according to the scope of claims. In addition, it should be noted that not all of the combinations of characteristics features described in the embodiment are necessary as means for solving the problems of the invention.

In the above embodiment, the case of applying the present invention to a multi-electrode catheter 1, which is a kind of medical devices, is explained. However, the present invention is not limited thereto, and it is also possible to apply the present invention to endoscopes, for example. The present invention may be applied to devices other than medical devices.

The invention claimed is:

1. An electric wire connection structure, comprising:
insulated electric wires each including a core and an insulation coating covering the core, the cores of the insulated electric wires being connected to pads provided on a substrate,
wherein the insulated electric wires are arranged with an interval that is less than an outer diameter of the insulated electric wire along a predetermined alignment direction and arranged parallel to each other,
wherein the insulation coating is removed at a part in a longitudinal direction of each of the insulated electric wires to expose the core, and exposed portions of the cores are connected to the pads, respectively,
wherein the exposed portion of the core is formed in an area except a tip end of each of the insulated electric wires,
wherein at least one of the insulated electric wires is configured in such a manner that the core is exposed in an area where the insulation coatings of adjacent ones of other insulated electric wires in the alignment direction are not removed.

2. The electric wire connection structure according to claim 1, wherein a space is formed between the insulated electric wires.

3. The electric wire connection structure according to claim 2, wherein an outer diameter of the core is 0.1 mm or less.

4. The electric wire connection structure according to claim 1, wherein the exposed portions of the cores are alternately aligned at a first position and a second position, with a predetermined interval in a direction perpendicular to the alignment direction.

5. A medical device, comprising:
a catheter cable comprising insulated electric wires each including a core and an insulation coating covering the core, and a substrate including pads connected to the cores of the insulated electric wires, one of both ends in a longitudinal direction of the catheter cable being configured to be inserted into a human body,
wherein the cores of the insulated electric wires are connected to the pads respectively by the electric wire connection structure according to claim 1.

6. The electric wire connection structure according to claim 1, wherein the interval of the insulated electric wires in the alignment direction is 20% or more and 80% or less of the outer diameter of the insulated electric wire.

7. An electrical wire connection method for connecting cores of insulated electric wires each including the core and an insulation coating covering the core with pads provided on a substrate, the method comprising:
holding the insulated electric wires at a point at a tip end in the longitudinal direction and a point distant from the tip end in the longitudinal direction, and aligning the insulated electric wires parallel to each other with an interval that is less than an outer diameter of the insulated electric wire along a predetermined alignment direction;
removing the insulation coating to expose the core in a part in a longitudinal direction of each of the insulated electric wires; and
arranging the insulated electric wires in such a manner that the alignment direction is parallel to the substrate and connecting the exposed cores to the pads, and connecting the cores of the insulated electric wires to the pads respectively, while a longitudinal tension is applied to the insulated electric wires,
wherein at least one of the insulated electric wires is configured in such a manner that the core is exposed in an area where the insulation coatings of adjacent ones of other insulated electric wires in the alignment direction are not removed, and
wherein, in the connecting, the cores of the insulated electric wires are connected to the pads respectively between the first point and the second point.

8. A method for manufacturing a medical device including a catheter cable including insulated electric wires each including a core and an insulation coating covering the core, and a substrate including pads connected to the cores of the insulated electric wires, one of both ends in a longitudinal direction of the catheter cable being configured to be inserted into a human body, the method comprising:
connecting the cores of the insulated electric wires to the pads respectively by the electric wire connection method according to claim 7.

* * * * *